(12) United States Patent
Steinthorsson et al.

(10) Patent No.: US 11,376,029 B2
(45) Date of Patent: Jul. 5, 2022

(54) COMPLIANT MECHANISM FOR PROVIDING STEPWISE CLICKING HAPTIC FEEDBACK

(71) Applicant: REON EHF., Reykjavik (IS)

(72) Inventors: Asthor Tryggvi Steinthorsson, Reykjavik (IS); Tim Horeman, Leidersorp (NL)

(73) Assignee: REON EHF., Reykjavik (IS)

( * ) Notice: Subject to any disclaimer, the term of this patent is extended or adjusted under 35 U.S.C. 154(b) by 77 days.

(21) Appl. No.: 16/651,408

(22) PCT Filed: Oct. 1, 2018

(86) PCT No.: PCT/IS2018/050010
§ 371 (c)(1),
(2) Date: Mar. 27, 2020

(87) PCT Pub. No.: WO2019/064317
PCT Pub. Date: Apr. 4, 2019

(65) Prior Publication Data
US 2020/0289139 A1 Sep. 17, 2020

(30) Foreign Application Priority Data
Sep. 29, 2017 (IS) .......................... 050190

(51) Int. Cl.
*A61B 17/29* (2006.01)
*A61B 34/00* (2016.01)

(52) U.S. Cl.
CPC .............. *A61B 17/29* (2013.01); *A61B 34/76* (2016.02); *A61B 2017/2902* (2013.01); *A61B 2017/2943* (2013.01)

(58) Field of Classification Search
CPC . A61B 17/29; A61B 34/76; A61B 2017/2902; A61B 2017/2943; A61B 2017/2901; A61B 2017/2939
See application file for complete search history.

(56) References Cited

U.S. PATENT DOCUMENTS

2014/0358029 A1 12/2014 Vetter
2016/0199121 A1 7/2016 Kase
2016/0220253 A1 8/2016 Martinez

FOREIGN PATENT DOCUMENTS

EP 1415600 A1 5/2004
WO 2016056908 A1 4/2016

OTHER PUBLICATIONS

International Search Report and Written Opinion dated Nov. 19, 2018 for corresponding International Application No. PCT/IS2018/050010.

(Continued)

*Primary Examiner* — Brooke Nicole Labranche
(74) *Attorney, Agent, or Firm* — Tarolli, Sundheim, Covell & Tummino LLP

(57) ABSTRACT

A compliant mechanism is provided, for extending a rod in a manually controlled instrument and providing clicking haptic feedback, such as in particular in a compliant surgical grasper. The compliant mechanism comprises an inner rod that comprises an upper slit and a lower slit running through a section of the rod, that forma generally S-shaped cut in the rod, such that when ends of the rod are pulled at the S-shaped form allows an extension of the rod in the axial direction by compliant bending; the mechanism comprises a notch placed on the outer surface of the rod, adjacent to a respective slit opening and on the proximal side of the opening, and an outer sleeve enclosing the inner rod, the sleeve having on its inner surface one or more groove or teeth facing the at least one notch on the rod surface, such (Continued)

(a)

(b)

that when the rod is extended, the notch engages with said groove or tooth to create a clicking haptic feedback.

23 Claims, 7 Drawing Sheets

(56) References Cited

OTHER PUBLICATIONS

Danish Search Report dated Dec. 12, 2017 for corresponding Application No. SE 2017 02582.
Stapel, A, and Herder, J.L. "Feasibility study of a fully compliant statically balanced laparoscopic grasper." ASME 2004 International Design Engineering Technical Conferences and Computers and Information in Engineering Conference. American Society of Mechanical Engineers Digital Collection, 2004.

(a)

(b)

(a)

(b)

(a)

(b)

COMPLIANT MECHANISM FOR PROVIDING STEPWISE CLICKING HAPTIC FEEDBACK

RELATED APPLICATIONS

The present application is a U.S. National Stage application under 35 USC 371 of PCT Application Serial No. PCT/IS2018/050010, filed on 1 Oct. 2018; which claims priority from IS Patent Application No. 050190, filed 29 Sep. 2017, the entirety of both of which are incorporated herein by reference.

FIELD

The invention is within the field of compliant mechanisms and in particular relates to a compliant mechanism and devices using such mechanism, wherein the mechanism allows for manually controlled linear movement and provides haptic feedback.

INTRODUCTION

Compliant mechanisms are being developed as alternatives to conventional hinge/joint-based movement in various devices, including surgical graspers, such as in particular laparoscopic graspers. Compliant graspers provide advantages such as in terms of compactness, no need for lubrication, ease of sterilization, etc. Compliant graspers are disclosed for example in Stapel A, Herder, J. L. *Feasibility Study of a Fully Compliant Statically Balanced Laparoscopic Grasper* Proceedings DETC'04 (DETC2004-57242), NL 2009202, and WO 03/026519.

A compliant mechanism such as a compliant grasper will typically have one particular resting position of the grasper jaws, which is maintained when no force is applied. This may be an open position, and then a force needs to be applied in order to move the jaws into a more open position or a closed position, and the applied force generally needs to be maintained to keep the grasper in the non-balanced position. This may cause fatigue in the hands of the surgeon. Another challenge in compliant mechanisms such as compliant graspers and other devices where accurate force transfer is of concern, is lack of intuitive force feedback, since the force transmission acts through elastic energy in the compliant parts. This means that the needed actuation force on the handle of a grasper is often not in an intuitive relation to the force being applied by the jaws. For example, when a delicate object is being gripped and held by the grasper, the force applied by the grasper jaws must be limited and accurately applied in order not the damage the object. This can be difficult when the force applied by the jaws is not the same as the actuation force applied on the grasper handle, and if the relationship therein is not linearly intuitive.

BRIEF DESCRIPTION OF FIGURES

The skilled person will understand that the drawings, described below, are for illustration purposes only. The drawings are not intended to limit the scope of the present teachings in any way.

SUMMARY

Figure 1:
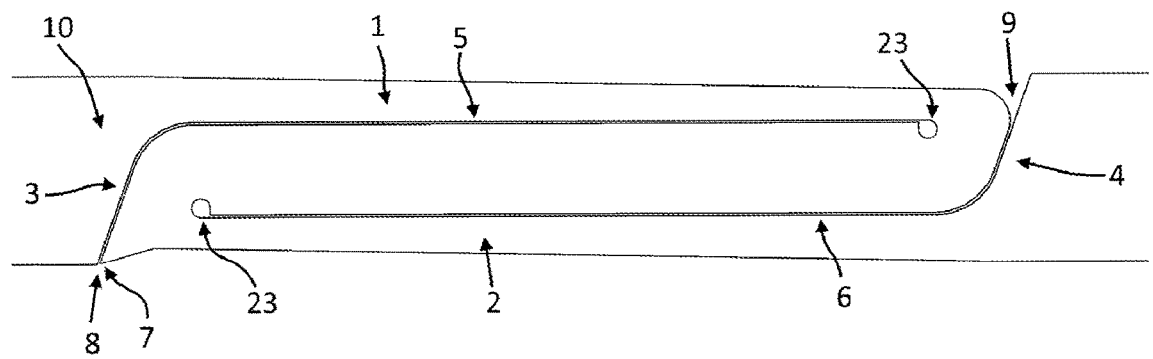
FIG. 1 shows a simplified example of the inner rod of a compliant mechanism according to one embodiment, panel (a) shows the resting position of the mechanism/rod, whereas in panel (b) both ends of the rod of the compliant mechanism are being pulled in opposite directions, resulting in an extension of the rod.
Figure 1:
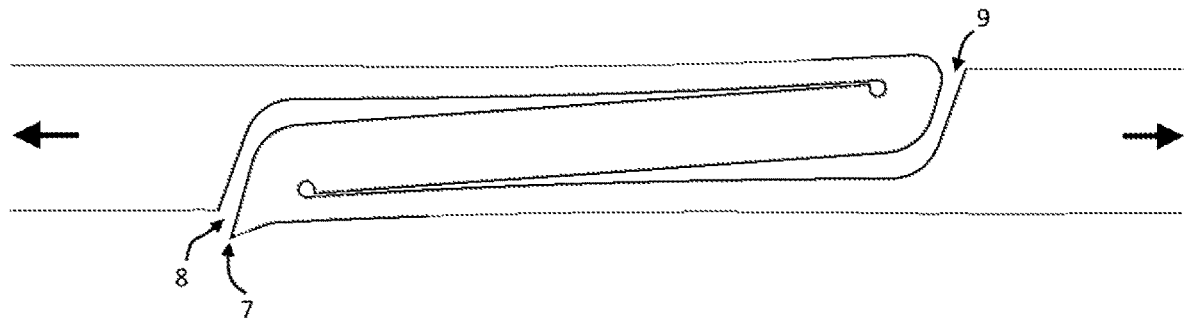

The invention relates to a compliant mechanism and devices using such mechanism, wherein the mechanism allows for manually controlled linear movement and extension of a generally linear member and provides stepwise click-type haptic feedback in response to movement and stops said movement after a certain displacement.

The mechanism is useful in manual instruments for precise force application such as medical graspers, both graspers with conventional hinge-based grasping mechanism ("alligator" type graspers) and in particular graspers with a compliant hinge-free grasping mechanism. The mechanism can also advantageously be used to place a force limit on such manual instruments.

In one aspect the invention provides a compliant mechanism for extending a rod in a manually controlled instrument and providing clicking haptic feedback, wherein the mechanism comprises:

an inner rod with a compliant section that comprises an upper slit and a lower slit, the slits running through the compliant section substantially along the axial direction of the inner rod, the slits each having on respective opposite ends a bent section that leads into a slit opening, the upper slit having an opening in a lower surface of the rod and the lower slit having an opening in an upper surface of the rod, thereby forming a generally S-shaped form in the compliant section in the rod, such that when one or both ends of the rod are pulled at in the axial direction, the S-shaped form allows an extension of the rod in the axial direction by compliant bending;

at least one notch placed on the outer surface of the rod, adjacent to a respective slit opening and on the proximal side of the opening with respect to the compliant section;

an outer sleeve enclosing the inner rod, the sleeve having on its inner surface one or more groove or teeth facing the at least one notch on the rod surface;

such that when the rod is extended, the notch engages with said groove or tooth to create a clicking haptic feedback.

In another aspect the invention sets forth a compliant mechanism for extending a rod in a manually controlled instrument and providing clicking haptic feedback, comprising:

an inner rod with a compliant section that comprises an outer slit and two inner slits, said slits running through the compliant section substantially along the axial direction of the rod and symmetrically arranged about the central axis of the rod, the outer slit being generally U-shaped and comprising two oppositely located outer axially extending sections that are joined via curved bends by a proximal section and having opposite distal ends that terminate each in a respective bore vertical to the axial direction of the rod, the inner slits being interior of the outer axially extending sections of the outer slit, each inner slit having a bent section that leads into a slit opening adjacent to one of said bores and a longitudinal section extending from the bent section towards the proximal section of the outer slit and terminating in a respective end bore vertical to the axial direction of the rod, thereby forming a double S-shaped form symmetrical about a central mirror plane of the rod, such that when one or both ends of the rod are pulled at in the axial direction, the double S-shaped form allows an extension of the rod in the axial direction by compliant bending;

at least one notch placed on the outer surface of the rod, adjacent to a respective slit opening and on the proximal side of the opening with respect to the compliant section;

an outer sleeve enclosing the inner rod, the sleeve having on its inner surface one or more groove or teeth facing the at least one notch on the rod surface, such that when the rod is extended, the notch engages with said groove or tooth to create a clicking haptic feedback.

Another aspect of the invention provides a compliant grasper, comprising at least two jaws that can be moved towards and away from each other, to hold and release an object in between the jaws, wherein the jaws are moved through a compliant bending mechanism, a handle for actuating the compliant bending mechanism, comprising at least a supported handle element and a movable handle element, an elongated mechanism for transferring movement actuation from the handle to the jaws, comprising a mechanism according to the present invention, for providing click-type haptic feedback in response to movement actuation through the handle.

In one embodiment the elongated mechanism comprises an elongated support member connecting the supported handle element and a supported connecting point of the jaws, and an elongated actuation rod connecting the movable handle element and a moveable connecting point of the jaws, wherein the elongated actuation rod comprises said inner rod of the compliant mechanism and the elongated support member comprises or is fixedly adjoined to the outer sleeve of the compliant mechanism.

DESCRIPTION

In the following, exemplary embodiments of the invention will be described, referring to the figures. These examples are provided to provide further understanding of the invention, without limiting its scope.

In the description herein the device is generally described with reference to a particular orientation in space, which should not be construed as limiting but is merely used for ease of describing the relative orientation of features and structural elements of the invention with respect to each other. Thus, for example the "upper" and "lower" slits 1,2 mentioned above are referred to with these terms as they are seen as upper and lower, respectively, when the mechanism/device is viewed from the side as in the accompanying figures, but it should be noted that the mechanism may as well be viewed "up-side down" relative to those figures, meaning that an "upper" element need not be above a "lower" element in an absolute sense.

The compliant mechanism of the invention is configured in a rod-like structure referred to herein as an "inner rod" 10, as it is generally enclosed by a sleeve part referred to as an "outer sleeve" 11. The inner rod 10 is preferably, but not limited to, a generally cylindrical shape.

The upper and lower slits 1,2 that form the compliant mechanism can also be described as cuts, that would generally lie in a straight or curved plane with at least one axis of the plane being horizontal, when viewing the mechanism from the side. Accordingly, the slits can be straight or curved and would typically but not necessarily both have the same shape except at the bent sections 3,4 described further below.

The extended sections 5,6 of the slits 1,2 are preferably straight and preferably parallel. The extended sections of the slits can lie in horizontal planes with respect to the mechanism/device, or in some embodiments the extended sections are straight and lie in planes that have a slight angle with respect to horizontal, such that the slits define planes each being inclined towards its respective slit opening at a mechanically efficient angle to the longitudinal axis of the rod. Said angle can be for example an angle in the range of 0.5° to 10°, such as a range from about 0.5° or from about 1.0° or from about 1.5°, to about 10°, or to about 9° or to about 8° or to about 7° or to about 6° or to about 5.0° or to about 4.0° or to about 3.0°. Preferably the slits define parallel planes having the same angle with respect to horizontal. An example of such parallel inclined slits is shown in FIG. 1. In some embodiments the two slits 1,2 are symmetrically formed about a central point, which by definition is the central point of the compliant section.

Thus, the slits 1,2 and slit openings 8,9 form a generally S-shaped form (or the mirror image thereof) in the compliant section when viewing from the side, such that when one or both ends of the rod 10 are pulled at axially in opposite directions, the S-shaped form allows an extension of the rod in the axial direction by compliant bending, in which the slits are forced to open up as illustrated in panel (b) of FIG. 1.

The bent sections 3,4 will typically each comprise at least a curved part and comprise each in some embodiments as well as straight part that leads into the respective slit opening.

The straight part is in some embodiments a angle in the range of 0–20° from vertical, such as at an angle in the range from about 0° or about 2° or about 5° to about 20° to about 15° or to about 10°. This means that the angle between each slit extended section 5,6 and its respective bent section straight part is typically an obtuse angle, such as preferably an angle in the range of about 95-120°, such as the range of about 95-110° or the range of about 100-110°, or the range of about 100-120°.

There is at least one notch 7 placed on the outer surface of the rod, adjacent to a respective slit opening 8 and on the proximal side of the opening with respect to the compliant section. The mechanism further comprises an outer sleeve 11 enclosing the inner rod 10. The sleeve has on its inner surface one or more groove or teeth facing the at least one notch on the rod surface, and when the rod is extended, the notch moves downwardly, towards the outer sleeve, and engages with one of said groove or teeth to create a clicking haptic feedback. Preferably the one or more groove or teeth comprise more than one groove or teeth, such as for example but not limited to two, three, four, five, six, or seven grooves or teeth.

The terms proximal and distal as used herein refer, unless otherwise indicated, to relative positions within the compliant mechanism of the invention, thus when two elements are referred to as proximal and distal (or proximally and distally arranged) the proximal elements is closer to the center point of the compliant mechanism than the distal element is.

The outer sleeve 11 typically has an inner tubular space with a cross section that fits around the cross section of the inner rod, making room for the notch 7 and groove or teeth to engage. Thus the cross-section of the inner space of the outer sleeve is in some embodiments circular, and in other embodiments with a different cross-section, such as but not limited to a generally square or rectangular cross-section, a hexagonal or octagonal cross-section, or a different cross-section suitable for the shape of the selected inner rod.

It follows that the one or more groove or teeth will include a most distal groove or tooth 13. In one embodiment the most distal groove or tooth has a shape that forms a generally inclined proximal surface 14 with an acute angle (relative to horizontal) that engages with said notch. This results in that when the notch engages with said groove or teeth, the inclined proximal surface prevents the notch from moving further distally.

Figure 2:
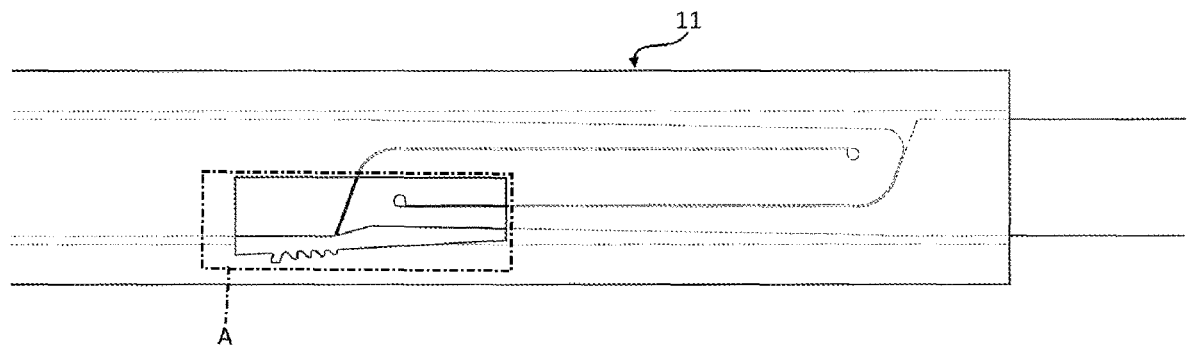
FIG. 2 illustrates a row of grooves in the outer sleeve of the mechanism for engaging with the notch proximally adjacent to a slit opening. The lower panel (b) shows a blow-up view of the notch and grooves that are exposed through the cut-out window 24.
Figure 2:
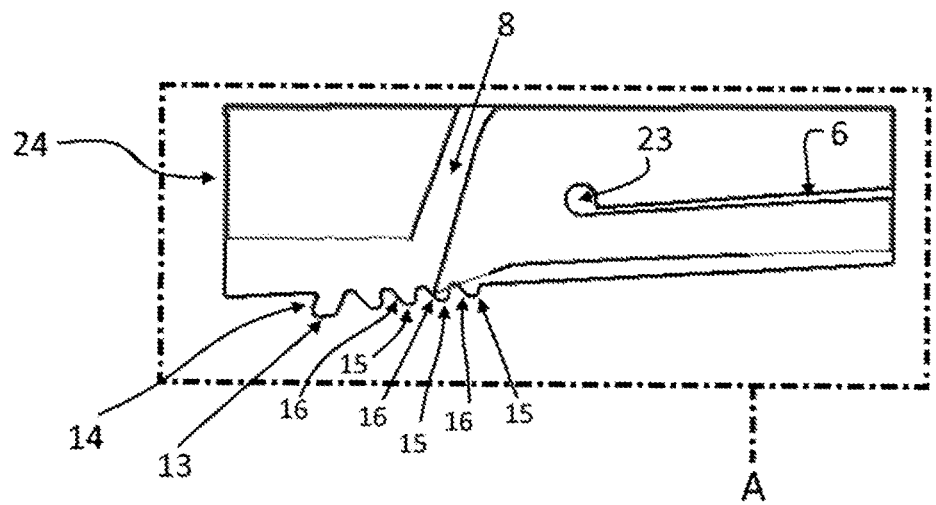

In some embodiments the one or more groove or teeth comprise or form a row of a plurality of grooves or teeth, such that as the rod is further extended said notch moves from one groove or tooth to the next, creating a stepwise clicking feedback. The row or plurality of grooves or teeth preferably comprise one or more proximal grooves or teeth 15 (meaning that they are all proximal to the most distal groove or tooth) that each have an inclined proximal surface 16 with an obtuse angle (relative to horizontal), allowing the notch to slide from a proximal groove or tooth to the next distally adjacent groove or tooth. This is illustrated in FIG. 2(*b*).

In some embodiments the one or more groove or teeth comprise a plurality of grooves or teeth that lie along a line that is inclined away from the central axis of the rod in the distal direction. One such embodiment is illustrated in FIG. 2, where it is seen that each groove/teeth is lower (with respect to horizontal) than its adjacent proximal neighbour ('lower' meaning farther from the horizontal central axis). This is done in particular to accommodate for the notch moving further downwardly as the rod is further extended.

Figure 3:
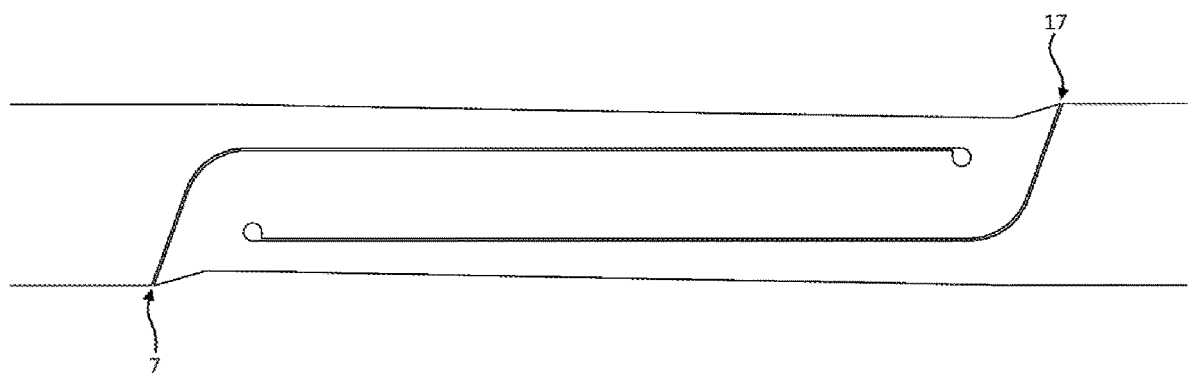
FIG. 3 shows an embodiment with two oppositely arranged notches on the inner rod, each one adjacent to a respective slit opening.

In some embodiments the mechanism comprises at least one notch 7 adjacent to the slit opening 8 of the lower slit 2, and at least one another notch 17 arranged oppositely on the inner rod, the another notch 17 being adjacent to the slit opening 9 of the upper slit 1. The outer sleeve in these embodiments has configured on its inner surface oppositely arranged sets of one or more teeth or grooves, respectively facing each of said at least one notches. This is illustrated in FIG. 3 (outer sleeve not shown). Such oppositely arranged sets of one or more teeth or grooves are in some embodiments arranged as a thread or a series of circular ring-shaped grooves around the perimeter of the inner space of the outer sleeve.

In some embodiments, each slit, at its end opposite the slit opening, terminates in a substantially circular bore 23 lying in the plane of the slit vertically to the central axis of the rod. Examples of this are illustrated in FIGS. 1-3. This serves to reduce the stress in the material immediately surrounding the terminating internal ends of the slits and to better distribute the shear forces.

FIG. 2 also shows an optional cut-out window or frame 24, which exposes the notch and teeth arrangement. This has the practical purpose of simplifying the manufacturing of the teeth/grooves in the outer sleeve, which in this way can be cut with wire-EDM (wire electric discharge machining). Thus, the window/frame 24 is hollow opening through the outer sleeve (through both sides of the sleeve), where the grooves/teeth are formed as part of the lower edge of the window/frame 24.

Figure 4:
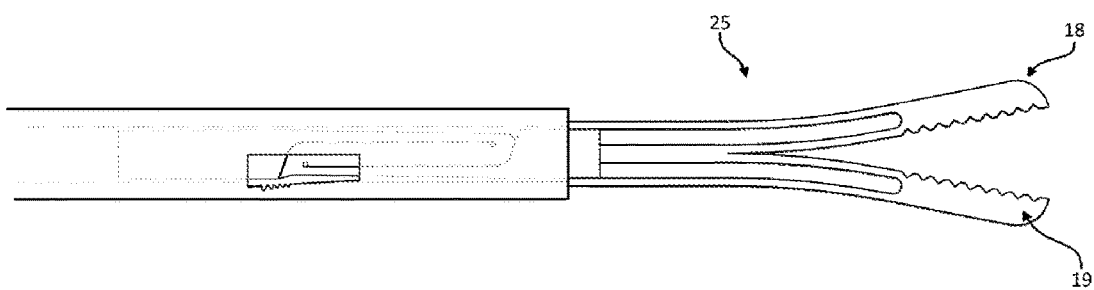
FIG. 4 illustrates how the compliant mechanism can be arranged within a compliant grasper.

As is understood from this disclosure, the compliant mechanism is particularly suitable for but not limited to forming a part in a surgical grasper instrument, wherein extension and retraction of an inner rod is coupled with opening and closing of the grasper jaws. The compliant mechanism is particularly useful in a compliant grasper, which refers to a grasper comprising a jointless compliant jaw mechanism. FIG. 4 illustrates how a compliant mechanism of the invention is incorporated into a compliant grasper 25, where the inner rod of the compliant mechanism is coupled with the force extending rod that transfers movement in order to open and close jaws 18, 19.

Figure 8:
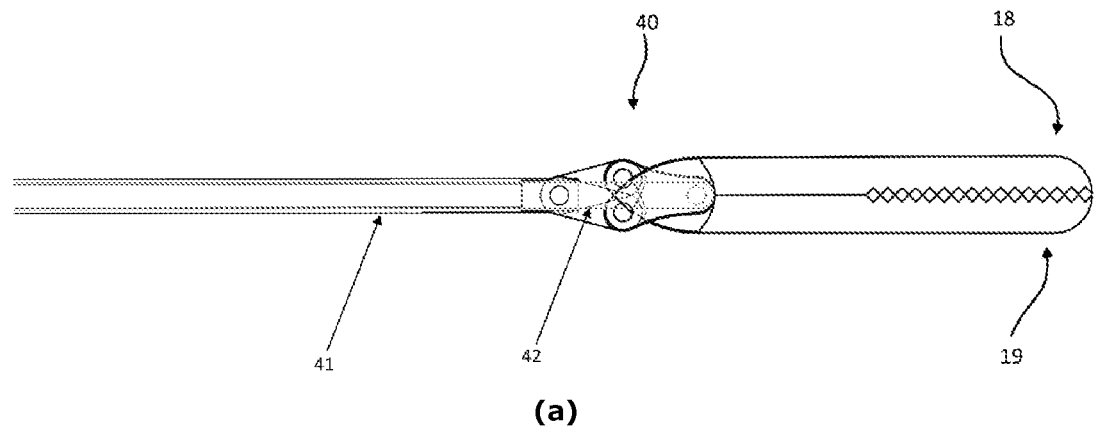
FIG. 8 shows the front portion of a alligator-type hinged grasper, in a closed position (a) and open position (b).
Figure 8:
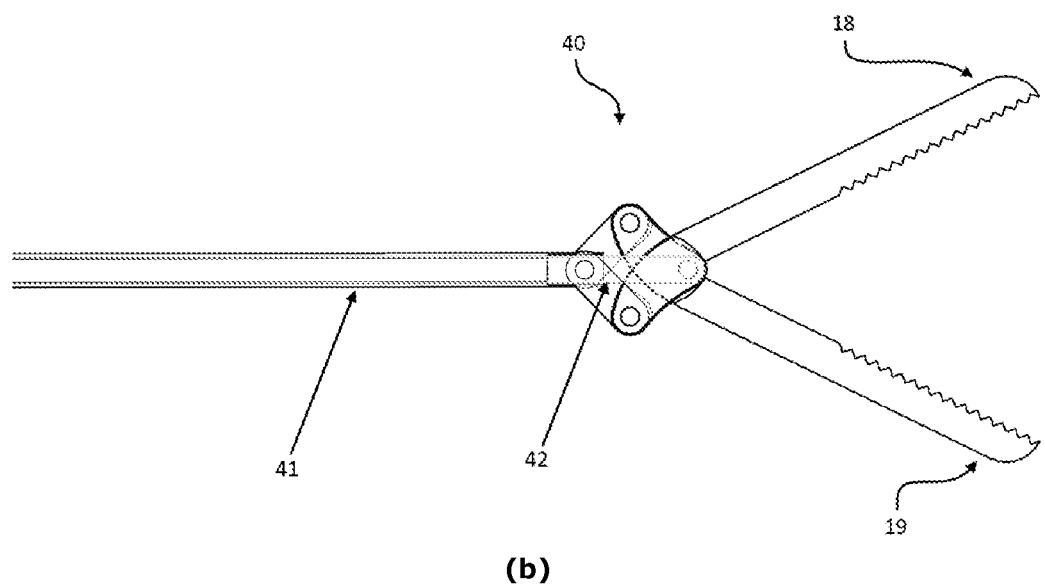

The compliant mechanism is however as well useful in some situations in conventional graspers (graspers with a conventional hinge-based grasping mechanism i.e. "alligator" type graspers, one example shown in FIG. 8). In some situations, such as when using a fine grasper for delicate applications where only a limited grasping force may be applied, it can be advantageous to have a haptic feedback click mechanism also in such conventional alligator graspers, to give a "click" signal when a certain amount of grasping is applied. In some embodiments a grasper of the invention (either a fully compliant grasper, or hinge-based grasper with a compliant haptic feedback mechanism of the invention) is configured so that applied force cannot be over a maximum limit, that is, after a certain "click" position is reached the grasper is locked from any further force being applied. The compliant mechanism of the invention can readily be arranged in a conventional type grasper that typically has a pair rods sliding relative to each other for extending the grasping motion. A compliant mechanism of the invention can be arranged as part of such mechanism, where the aforementioned sliding rods are configured to function as the inner rod and outer sleeve of the compliant mechanism of the invention. Such embodiment is illustrated in FIG. 9 with sliding rods 41 and 42 coupled to hinge mechanism 40 and compliant mechanism 43.

A surgical compliant grasper comprising a compliant mechanism according to the invention is accordingly also provided by the invention. The grasper comprises at least two jaws 18,19 that can be moved towards and away from each other in a generally conventional fashion, to hold and release an object in between the jaws. In one embodiment the jaws are moved through a compliant bending mechanism, as is known in the art.

Figure 7:
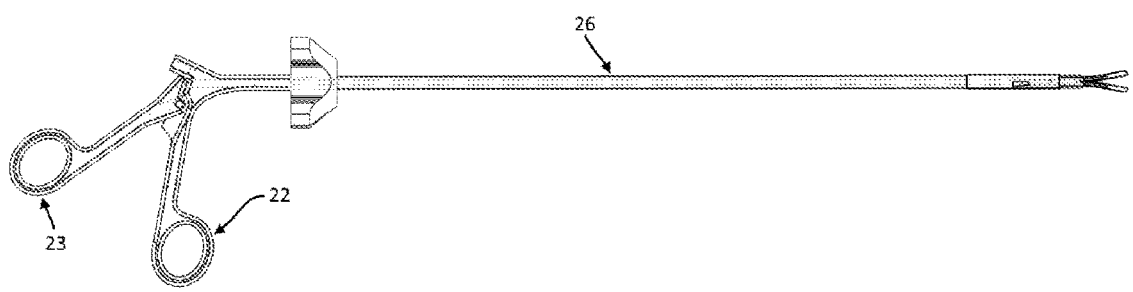
FIG. 7 shows a compliant grasper of the invention.

The grasper 25 comprises a handle for actuating the compliant bending mechanism, comprising at least a supported handle element 22 and a movable handle element 23. The term "supported" in this context is used as is customary in the field of compliant mechanics, referring to fixed point of reference. The grasper further comprises an elongated mechanism 26 for transferring movement actuation from the handle 22,23 to the jaws 18,19 and this elongated mechanism comprises a compliant mechanism as described above. In one embodiment the elongated mechanism comprises an elongated support member connecting the supported handle element 22 and a supported connecting point 21 (or points) of the jaws, and an elongated actuation rod connecting the movable handle element and a moveable connecting point 20 of the jaws, wherein the elongated actuation rod comprises said inner rod of the compliant mechanism. The elongated support member comprises or is fixedly adjoined to the outer sleeve of the compliant mechanism. One example of a grasper of the invention is depicted in FIG. 7.

Figure 9:
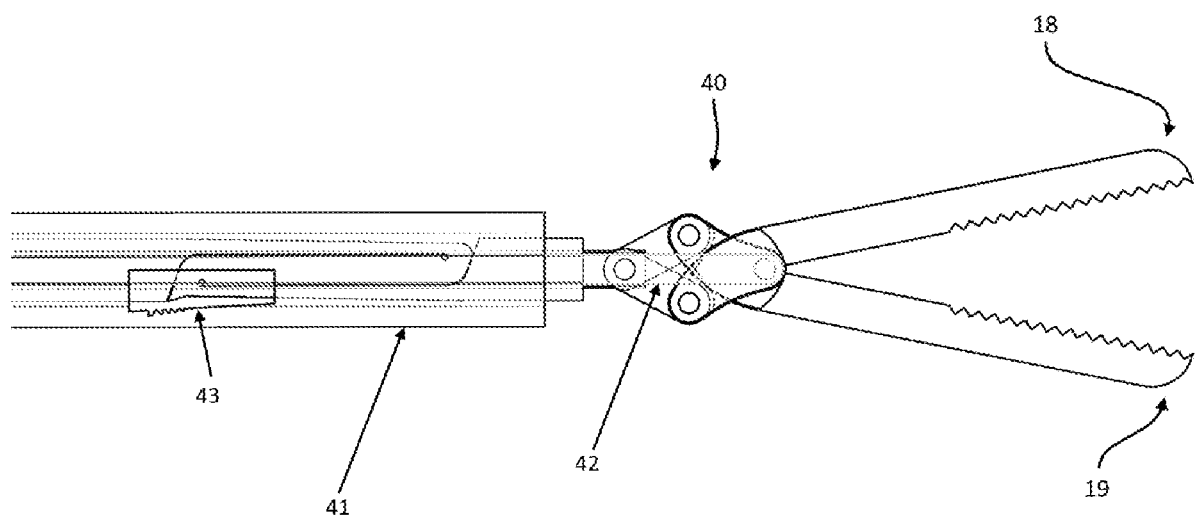
FIG. 9 shows a alligator-type hinged grasper with a compliant mechanism of the invention.

In another embodiment of a grasper of the invention, the jaws are moved with a conventional hinge-type "alligator" mechanism as shown in FIGS. 8 and 9; in this embodiment the compliant mechanism is arranged as part of sliding parallel rods 41, 42 in the grasper that extend movement from handles (not shown) to the grasper jaws 18, 19 through a hinge mechanism 40. The general connection between the sliding rods, hinge mechanism and jaws is illustrated in FIG. 8, (closed (a), and open (b) position), FIG. 9 illustrates how a compliant mechanism 43 is incorporated into the rod parts.

Figure 5:
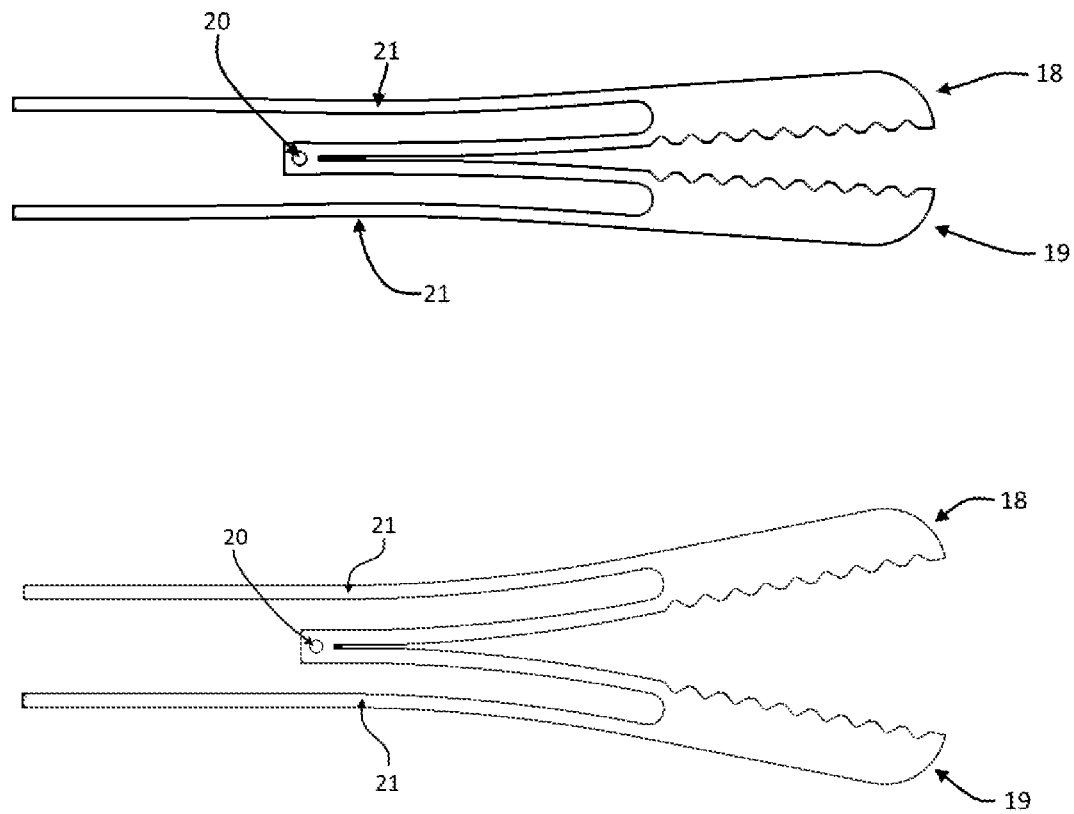
FIG. 5 shows the jaw portion of a compliant grasper of the invention, in a less open and more open position.

FIG. 5 shows a schematic example of jaws of a grasper of the invention, with a central connection point and two symmetric connecting points, in certain embodiments the central point serves as the moveable connecting point 20 as described above and the symmetric connecting points are supported connecting points 21, whereas in other embodiments the central connection point can be the supported connection point.

Figure 6:
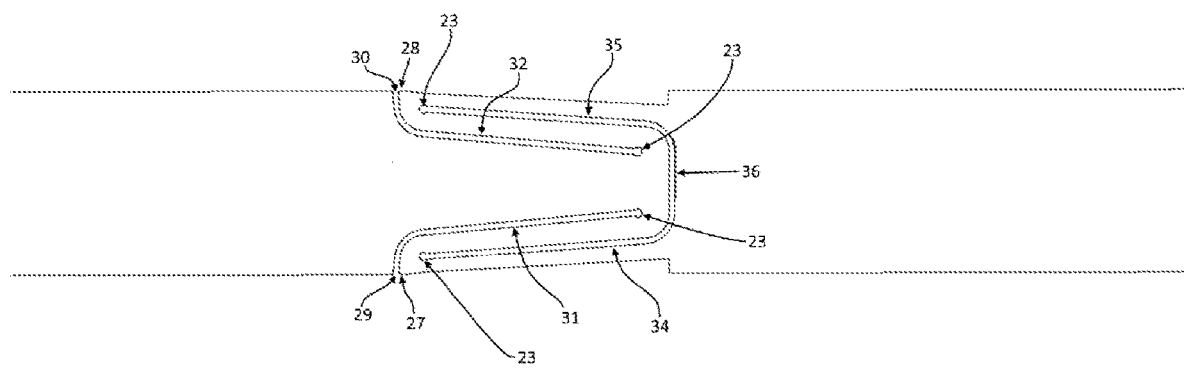
FIG. 6 shows an example of a "double S-Shape" compliant mechanism of the invention.
Figure 6:
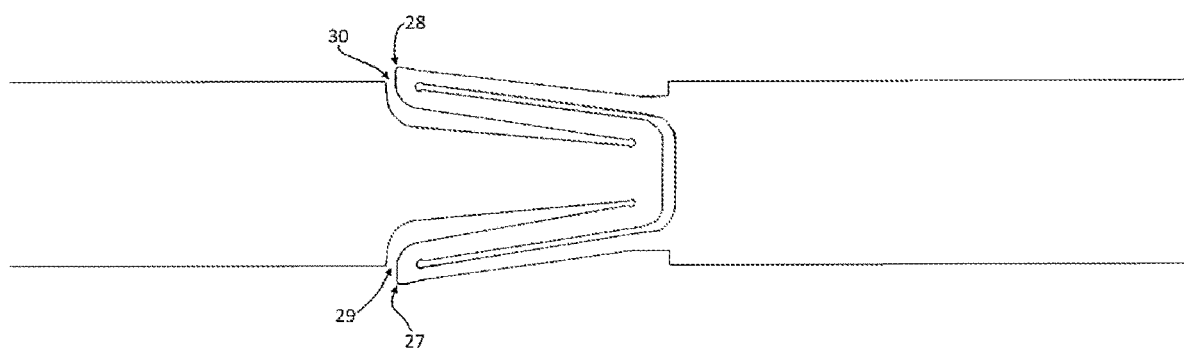

The "double S-shape" compliant mechanism of the invention is a version of the invention derived from the simpler S-shape mechanism. The "double S-shape" mechanism can be viewed as a combination of two of the simpler S-shapes put together, symmetrically about a central horizontal axis of the mechanism/device. An illustration of the "double S-shape" mechanism is shown in FIG. 6. The double-S mechanism can have one notch 27, on either the upper or lower side, for engaging with teeth or grooves, as explained above, or at least two notches 27,28, wherein at least one notch adjacent to each respective slit opening 29,30. The slit openings, notches and engaging teeth/grooves can be suitably symmetrically arranged, as the upper and lower slit openings 29,30 of the "double S-shape" mechanism are on the same side (left/right), in contrast to the simpler ("single S-shape") mechanism described in detail above, where the slit openings 8,9 are on opposite ends of the mechanism. The "double S-shape" mechanism can be described as comprising of two symmetric inner slits 31-32, each extending from an inner bore 23 to a respective slit opening 29,30 and a generally U-shaped outer slit 33 with two symmetric extending parts 34,35 extending from a respective bore 23 and joined by a central part 36. Panel (b) of FIG. 6 shows how the rod is extended through bending of the "double S-shape" mechanism.

As used herein, including in the claims, singular forms of terms are to be construed as also including the plural form and vice versa, unless the context indicates otherwise. Thus, it should be noted that as used herein, the singular forms "a," "an," and "the" include plural references unless the context clearly dictates otherwise.

Throughout the description and claims, the terms "comprise", "including", "having", and "contain" and their variations should be understood as meaning "including but not limited to", and are not intended to exclude other components.

The present invention also covers the exact terms, features, values and ranges etc. in case these terms, features, values and ranges etc. are used in conjunction with terms such as about, around, generally, substantially, essentially, at least etc. (i.e., "about 3" shall also cover exactly 3 or "substantially constant" shall also cover exactly constant).

The term "at least one" should be understood as meaning "one or more", and therefore includes both embodiments that include one or multiple components. Furthermore, dependent claims that refer to independent claims that describe features with "at least one" have the same meaning, both when the feature is referred to as "the" and "the at least one".

It will be appreciated that variations to the foregoing embodiments of the invention can be made while still falling within the scope of the invention can be made while still falling within scope of the invention. Features disclosed in the specification, unless stated otherwise, can be replaced by alternative features serving the same, equivalent or similar purpose. Thus, unless stated otherwise, each feature disclosed represents one example of a generic series of equivalent or similar features.

Use of exemplary language, such as "for instance", "such as", "for example" and the like, is merely intended to better illustrate the invention and does not indicate a limitation on the scope of the invention unless so claimed. Any steps described in the specification may be performed in any order or simultaneously, unless the context clearly indicates otherwise.

All of the features and/or steps disclosed in the specification can be combined in any combination, except for combinations where at least some of the features and/or steps are mutually exclusive. In particular, preferred features of the invention are applicable to all aspects of the invention and may be used in any combination.

The invention claimed is:

1. A compliant mechanism for extending an inner rod in a manually controlled instrument and providing clicking haptic feedback, comprising:
   an inner rod with a compliant section that comprises an upper slit and a lower slit, the slits running through the compliant section substantially along the axial direction of the inner rod, the slits each having on respective opposite ends a bent section that leads into a slit opening such that the upper slit has an opening in a lower surface of the inner rod and the lower slit has an opening in an upper surface of the inner rod, thereby forming a generally S-shaped form in the compliant section in the inner rod, such that when one or both ends of the inner rod are pulled at in the axial direction, the S-shaped form allows an extension of the inner rod in the axial direction by compliant bending;
   at least one notch placed on a surface of the inner rod, adjacent to either of the slit openings and on the proximal side of either of the slit openings with respect to the compliant section;
   an outer sleeve enclosing the inner rod, the sleeve having on its inner surface one or more grooves or teeth facing the at least one notch on the surface of the inner rod, such that when the inner rod is extended, the at least one notch engages with the one or more grooves or teeth to create a clicking haptic feedback.

2. The compliant mechanism of claim 1, wherein at least a most distal groove or tooth comprised in the one or more grooves or teeth has a shape that forms a generally inclined proximal surface with an acute angle that engages with the at least one notch.

3. The compliant mechanism of claim 1, wherein the one or more grooves or teeth comprise or form a row of a plurality of grooves or teeth, such that when the rod is further extended, the at least one notch moves from one groove or tooth to the next, creating a stepwise clicking feedback.

4. The compliant mechanism of claim 3, wherein one or more proximal grooves or teeth of the plurality of grooves or teeth have each an inclined proximal surface with an obtuse angle, such that as the rod is extended, the at least one notch slides from a proximal groove or tooth to the next distally adjacent groove or tooth.

5. The compliant mechanism of claim 1, wherein the one or more grooves or teeth comprise a plurality of grooves or teeth that lie along a line that is inclined away from the central axis of the rod in the distal direction such that the most distal groove or tooth is at a position farther from the central axis of the rod than the most proximal groove or tooth, measured vertically from the central axis.

6. The compliant mechanism of claim 1, wherein the at least one notch comprises one notch adjacent to the slit opening of the lower slit, and another notch adjacent to the slit opening of the upper slit, wherein the sleeve has on its inner surface a thread or opposite rows of teeth or grooves, to engage with both notches.

7. The compliant mechanism of claim 1, wherein the upper and lower slits are essentially parallel.

8. The compliant mechanism of claim 1, wherein the slits define planes each being inclined towards its respective slit opening at a mechanically efficient angle to the longitudinal axis of the rod.

9. The compliant mechanism of claim 8, wherein the mechanically efficient angles are within a range from about 0.5° to 10°.

10. The compliant mechanism of claim 8, wherein the mechanically efficient angles are within a range from about 1° to 5°.

11. The compliant mechanism of claim 1, wherein each slit at its end opposite the slit opening terminates in a substantially circular bore lying in the plane of the slit vertically to the central axis of the rod.

12. The compliant mechanism of claim 1, wherein the two slits are symmetrical about a central point of the compliant section.

13. The compliant mechanism of claim 1, forming part of a surgical grasper instrument, wherein extension and retraction of the rod is coupled with opening and closing of jaws of the grasper.

14. The compliant mechanism of claim 13, wherein the surgical grasper instrument comprises a jointless compliant jaw mechanism.

15. The compliant mechanism of claim 13, wherein the surgical grasper instrument comprises a hinge-based alligator jaw mechanism.

16. A grasper instrument comprising
at least two jaws that can be moved towards and away from each other, to hold and release an object in between the jaws,
a handle for actuating the compliant mechanism of claim 1, comprising at least a supported handle element and a movable handle element,
an elongated mechanism for transferring movement actuation from the handle to the jaws, comprising the compliant mechanism of claim 1, for providing click-type haptic feedback in response to movement actuation through the handle.

17. The grasper instrument according to claim 16, which is a compliant grasper, wherein the jaws are moved through the compliant mechanism.

18. The grasper instrument according to claim 16, wherein the jaws are moved through a hinge-based alligator-type mechanism.

19. The grasper instrument according to claim 16, wherein the elongated mechanism comprises an elongated support member connecting the supported handle element and a supported connecting point of the jaws, and an elongated actuation rod connecting the movable handle element and a moveable connecting point of the jaws, wherein the elongated actuation rod comprises the inner rod of the compliant mechanism and the elongated support member comprises or is fixedly adjoined to the outer sleeve of the compliant mechanism.

20. A compliant mechanism for extending an inner rod in a manually controlled instrument and providing clicking haptic feedback, comprising:
an inner rod with a compliant section that comprises an outer slit and two inner slits, the slits running through the compliant section substantially along the axial direction of the rod and symmetrically arranged about the central axis of the rod, the outer slit being generally U-shaped and comprising two oppositely located outer axially extending sections that are joined via curved bends by a proximal section and having opposite distal ends that terminate each in a respective bore vertical to the axial direction of the rod, the inner slits being interior of the outer axially extending sections of the outer slit, each inner slit having a bent section that leads into a slit opening adjacent to one of the bores and a longitudinal section extending from the bent section towards the proximal section of the outer slit and terminating in a respective end bore vertical to the axial direction of the rod, thereby forming a double S-shaped form symmetrical about a central mirror plane of the rod,
such that when one or both ends of the rod are pulled at in the axial direction, the double S-shaped form allows an extension of the rod in the axial direction by compliant bending;
at least one notch placed on a surface of the inner rod, adjacent to either of the slit openings and on the proximal side of either of the slit openings with respect to the compliant section;
an outer sleeve enclosing the inner rod, the sleeve having on its inner surface one or more grooves or teeth facing the at least one notch on the surface of the inner rod, such that when the rod is extended, the notch engages with the one or more grooves or teeth to create a clicking haptic feedback.

21. The compliant mechanism according to claim 20, wherein the outer axially extending sections of the outer slit are inclined at an angle with respect to the central axis of the rod, from the curved bends towards the outer surface of the rod, in the range of 1° to 10°.

22. The compliant mechanism according to claim 20 wherein the longitudinal sections of the inner slits are inclined at an angle with respect to the central axis of the rod, from the end bores towards the bent sections, in the range of 1° to 10°.

23. The compliant mechanism according to claim 20 wherein the outer axially extending sections of the outer slit and the longitudinal sections of the inner slits are inclined at the same angle such that each outer axially extending section of the outer slit is parallel to the longitudinal section of its adjacent inner slit.

* * * * *